US00PP27956P2

(12) United States Plant Patent
Boughen

(10) Patent No.: US PP27,956 P2
(45) Date of Patent: May 2, 2017

(54) ***CORNUS* PLANT NAMED 'BYBOUGHEN'**

(50) Latin Name: *Cornus alba*
Varietal Denomination: Byboughen

(71) Applicant: Ron Boughen, Valley River (CA)

(72) Inventor: Ron Boughen, Valley River (CA)

(73) Assignee: Bylands Nurseries, Ltd., West Kelowna (CA)

( * ) Notice: Subject to any disclaimer, the term of this patent is extended or adjusted under 35 U.S.C. 154(b) by 33 days.

(21) Appl. No.: 14/756,238

(22) Filed: Aug. 19, 2015

(51) Int. Cl.
*A01H 5/00* (2006.01)

(52) U.S. Cl.
USPC ..... Plt./220

(58) Field of Classification Search
USPC ..... Plt./220
See application file for complete search history.

(56) References Cited

PUBLICATIONS

Svendsen Rural Roots Dogwoods I have known 2015 retrieved on Nov. 1, 2016, retrieved on the Internet at <http://www.lamediatheque.tc/wp-content/uploads/pdf/04RR_20150528.pdf> one page.*

Zimmerman Open-line Garden Show Podcast; Woody Plant Introductions for 2015, retrieved on Nov. 1, 2016, retrieved from the Internet at <http://open-linegardenshow.blogspot.com/2014/11/podcast-woody-plant-introductions-for.html> pp. 1-3, Nov. 2014.*

* cited by examiner

*Primary Examiner* — June Hwu
(74) *Attorney, Agent, or Firm* — Penny J. Aguirre

(57) ABSTRACT

A new cultivar of *Cornus*, 'Byboughen', characterized by its dwarf growth habit, its upright and rounded plant habit, its yellow-green foliage that turns golden yellow and suffused with red-purple in fall, and its stems that are bright coral red in winter.

2 Drawing Sheets

Botanical classification: *Cornus alba*.
Variety denomination: 'Byboughen'.

BACKGROUND OF THE INVENTION

The present invention relates to a new and distinct cultivar of *Cornus alba*, and will be referred to hereafter by its cultivar name, 'Byboughen'. 'Byboughen' is a new cultivar of red twig dogwood, a shrub grown for use as an ornamental landscape plant.

The Inventor discovered the new cultivar as naturally occurring branch mutation of *Cornus alba* 'Morden Amber' (not patented). 'Byboughen' was discovered amongst rooted cuttings that had been planted in a production field in Valley River, Manitoba, Canada in summer of 2009.

The Inventor discovered the new cultivar amongst rooted cuttings of *Cornus alba* 'Morden Amber' (not patented) that had been planted in a production field in Valley River, Manitoba, Canada in summer of 2009. The new cultivar is therefore a naturally occurring branch mutation of 'Morden Amber'.

Asexual propagation of the new cultivar was first accomplished by the Inventor by softwood stem cuttings in summer of 2011 in Valley River, Manitoba, Canada. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'Byboughen' as unique cultivar of *Cornus*.

1. 'Byboughen' exhibits a dwarf growth habit.
2. 'Byboughen' exhibits an upright and rounded plant habit.
3. 'Byboughen' exhibits yellow-green foliage.
4. 'Byboughen' exhibits stems that are bright coral red in winter.
5. 'Byboughen' exhibit fall foliage that is golden yellow and becomes suffused with red-purple.

The parent plant of 'Byboughen', 'Morden Amber', differs from 'Byboughen' in being larger in size (40% greater height and width). 'Byboughen' can also be compared to the *Cornus alba* cultivars 'Prairie Fire' (not patented), 'Bailhalo' (U.S. Plant Pat. No. 8,722), and 'Regnzam' (not patented). 'Prairie Fire' is similar to 'Byboughen' in having yellow-green foliage but differs from 'Byboughen' in being larger in size (2 m in height and 1.5 m in width). 'Bailhalo' and 'Regnzam' are similar to 'Byboughen' in having a dwarf growth habit. 'Bailhalo' differs from 'Byboughen' in having variegated foliage and 'Regnzam' differs from 'Byboughen' in having green foliage.

BRIEF DESCRIPTION OF THE DRAWINGS

The accompanying colored photographs were taken in mid summer and illustrate the overall appearance and distinct characteristics of 3 year-old plants the new *Cornus* as grown in a trial plot in West Kelowna, British Columbia, Canada.

The photograph in FIG. 1 provides a close-up view of a row of plants of 'Byboughen' in summer.

Figure 1:
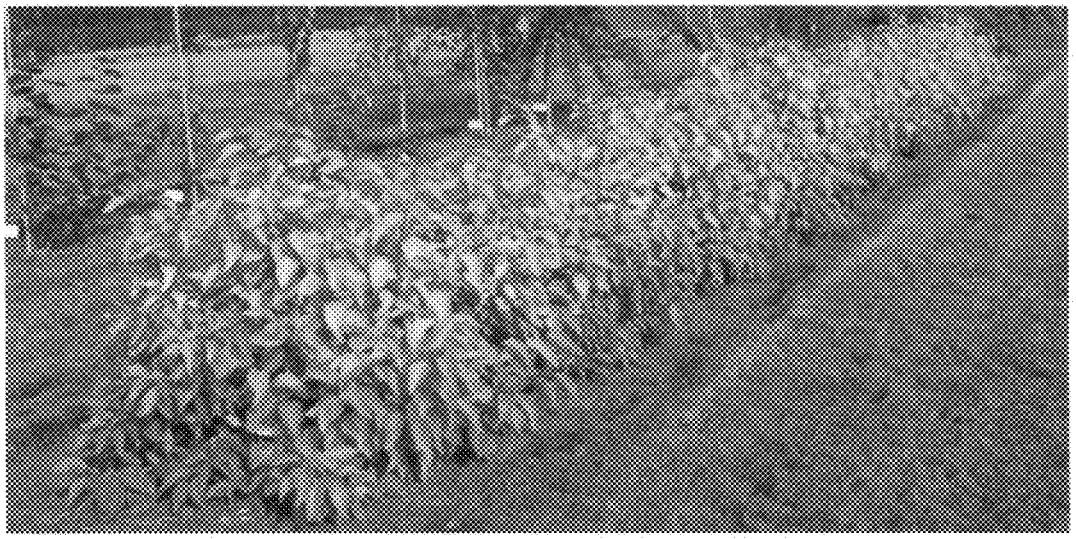
Figure 2:
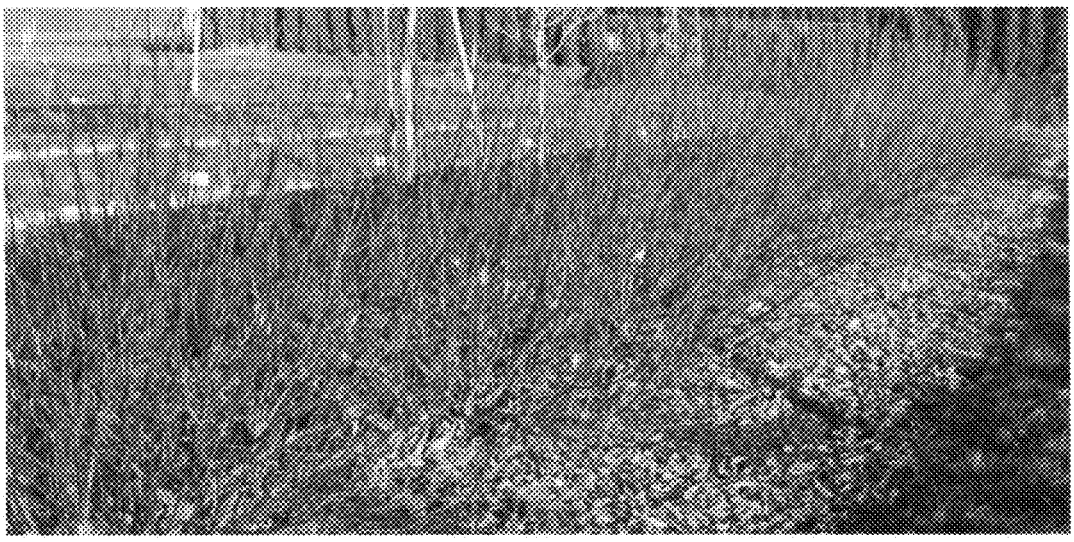

The photograph in FIG. 2 provides a view of a row of plants 'Byboughen' in winter.

Figure 3:
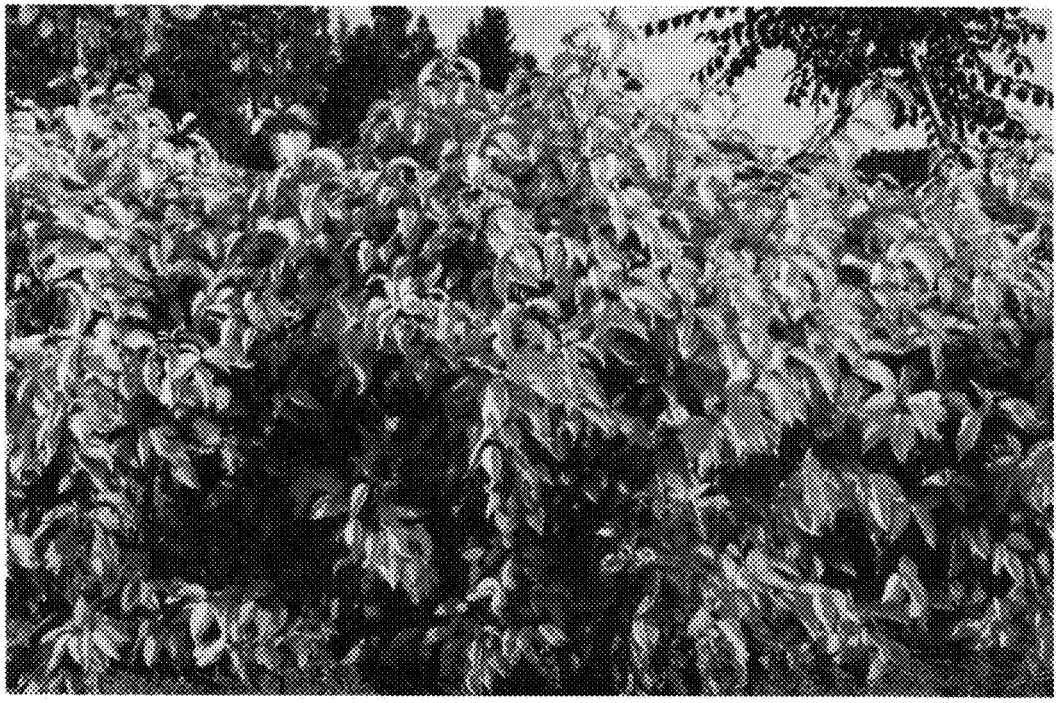

The photograph in FIG. 3 provides a view of the fall foliage of 'Byboughen'.

Figure 4:
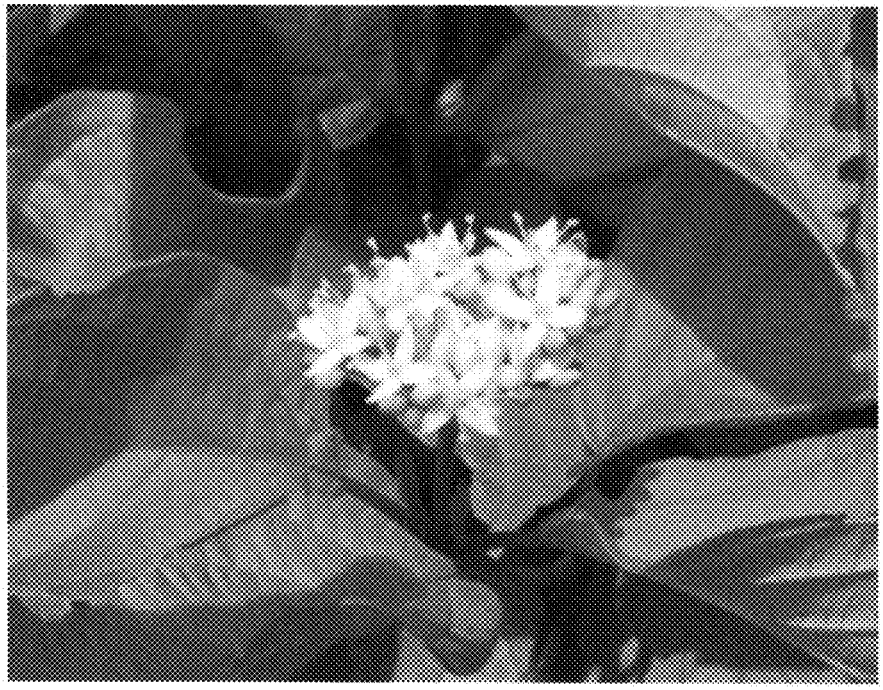

The photograph in FIG. 4 provides a view of an inflorescence of 'Byboughen'.

The colors in the photographs may differ slightly from the color values cited in the detailed botanical description, which accurately describe the colors of the new *Cornus*.

DETAILED BOTANICAL DESCRIPTION

The following is a detailed description of 1.5 year-old plants the new *Cornus* as grown in 2-gallon containers (from a 50-cell plug) in West Kelowna, British Columbia, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for 3 weeks in British Columbia, Canada.

*Plant type.*—Deciduous shrub.

*Plant habit.*—Dwarf, upright and rounded.

*Plant height and spread.*—Reaches 1.2 m in height and spread.

*Diseases and pests.*—No disease or pest resistance or susceptibility has been observed.

*Cold hardiness.*—At least in U.S.D.A. Zone 3.

*Root description.*—Fibrous, color 165C.

*Propagation*—Softwood stem cuttings.

*Growth rate.*—Moderate.

*Root development.*—Roots initiate in 21 days and fully develop in a 50-cell plug in 2 months.

Branch description:

*Branch shape.*—Round.

*Branch color.*—New twigs; a blend of N144A and 144A, mature branches; a blend of 161A and N144A and 144A, bark at base; a blend of 165A and 165B, winter color; primarily 45A.

*Branch size.*—Main branches; 5 mm in diameter, 10 cm above the soil level, lateral branches; average of 5 mm in diameter and 12 cm in length, secondary branches; up to 15 cm in length and 3 mm in diameter.

*Branch surface.*—New growth and mature branches glabrous, older bark; relatively smooth.

*Internode length.*—An average of 2 cm on lateral and secondary branches.

*Branching.*—Main stems; average of 4, lateral branches; average of 3, secondary branches; average of 2 per lateral branch.

*Lenticels.*—An average of 20 per branch 4 cm in length, rounded to oval in shape, an average of 1 mm in diameter, 158A in color.

Foliage description:

*Leaf shape.*—Elliptic.

*Leaf division.*—Simple.

*Leaf base.*—Cuneate.

*Leaf apex.*—Acuminate.

*Leaf fragrance.*—None.

*Leaf venation.*—Pinnate, color matches leaf coloration on upper surface and lower surface.

*Leaf margins.*—Very slightly undulated to entire.

*Leaf arrangement.*—Opposite.

*Leaf attachment.*—Petiolate.

*Leaf surface.*—Glabrous on upper surface and lower surface.

*Leaf size.*—Up to 12 cm in length and 5 cm in width.

*Leaf color.*—Leaves exposed to sun; young and mature leaves upper and lower surface a color between 1B and N144B, leaves that are shaded or on plants not grown in full sun; young and mature leaves upper surface; 144C, young and mature leaves lower surface; a color between 144B and 144C, fall color upper and lower surface; a blend of 162A and 11A becoming suffused with 187A to 187C.

*Petioles.*—Up to 2 cm in length and 1.5 mm in width, 144B in color and can be slightly suffused with 165A, glabrous surface.

*Stipules.*—Lanceolate in shape, 2 mm in length and 1 mm in width, 144B in color and suffused with spots of 177A.

*Lenticels.*—Slightly covered with minute raised lenticels average of 0.5 mm in diameter and 158C in color.

*Dormant leaf buds.*—4 to 6 mm in length and 3 mm in width, triangular to spatulate in shape, a blend of 15A and 177A in color.

Inflorescence description:

*Inflorescence type.*—Compound corymb on terminals.

*Inflorescence size.*—An average of 2 cm in length and 3.5 cm in diameter.

*Flower buds.*—Oblong-conical in shape, 155B in color with base 144D, an average of 2.5 mm in length and 1.5 mm in width.

*Flower fragrance.*—None.

*Lastingness of inflorescence.*—Inflorescence blooms for about 10 days with individual flowers lasting about 4 days.

*Flower quantity.*—Average of 60 flowers per inflorescence.

*Flower type.*—Rotate.

*Flower size.*—Average of 6.5 mm in diameter and 5 mm in depth.

*Peduncles.*—Primary an average of 1.3 cm in length to base of inflorescence and 2.5 mm in diameter with secondary an average of 1 cm in length and 2 mm in width and tertiary an average of 6 mm in length and 1.5 mm in width, 144C in color, slightly pubescent surface, oval in shape.

*Pedicels.*—Average of 2.5 mm in length and 1 mm in diameter, 144C in color, pubescent surface, oval in shape.

*Calyx.*—Closed campanulate in shape, 1.5 mm in diameter and length.

*Sepals.*—4, entirely fused into calyx, 146B in color, finely pubescent surface.

*Petals.*—4, base fused to top of calyx, spreading horizontally, lanceolate in shape, about 3 mm in length and 2 mm in width, margins entire, apex acute, outer and inner surface is glabrous, color of inner and outer surface is NN155B.

Reproductive organs:

*Gynoecium.*—1 pistil, style is about 2 mm in length, and 145C in color, stigma is about 0.5 mm in diameter, globose in shape and 145C in color, ovary is disked shape, about 1.5 mm in diameter and 145D in color.

*Androcoecium.*—4 stamens, about 5 mm in length, exserted beyond corolla, filaments are 155B in color and about 4 mm in length, anthers are about 1.5 mm in length, dorsifixed, 145C in color, pollen is moderate in quantity and 4D in color.

*Fruit and seed.*—True berry, oblong in shape, about 7 mm in length and 5 mm in diameter, present in mid summer, matures to 157C in color with a hint of 97B, seed; quantity 1, 5 mm in length and 4 mm in width in size and 199A in color.

It is claimed:

1. A new and distinct cultivar of *Cornus* plant named 'Byboughen' as herein illustrated and described.

* * * * *